United States Patent [19]

Makino et al.

[11] Patent Number: 5,362,910
[45] Date of Patent: Nov. 8, 1994

[54] GERMICIDAL AND FUNGICIDAL AGENT AND A GERMICIDAL AND FUNGICIDAL METHOD

[75] Inventors: Masahiro Makino, Sabae; Mikihiko Kurose, Fukui; Yoshihiro Sasada, Takefu, all of Japan

[73] Assignee: Nicca Chemical Co., Ltd., Fukui, Japan

[21] Appl. No.: 918,090

[22] Filed: Jul. 24, 1992

[30] Foreign Application Priority Data

Oct. 8, 1991 [JP] Japan .................................. 3-289112
Oct. 15, 1991 [JP] Japan .................................. 3-295093

[51] Int. Cl.$^5$ ..................... C07C 211/63; A01N 33/12
[52] U.S. Cl. ..................... 564/285; 564/282; 564/287; 564/288; 564/289; 564/292
[58] Field of Search ............... 564/282, 287, 288, 289, 564/292; 514/643, 642

[56] References Cited

U.S. PATENT DOCUMENTS

| | | | |
|---|---|---|---|
| 2,547,965 | 4/1951 | Olin | 260/567.6 |
| 2,666,010 | 1/1954 | Stayner | 167/30 |
| 2,812,350 | 11/1957 | Niederhauser | 260/501 |
| 3,231,509 | 1/1966 | Shema | 252/177 |
| 3,328,464 | 6/1967 | Gündel et al. | 260/567.6 |
| 3,576,873 | 4/1971 | Crounse | 260/567.6 |

FOREIGN PATENT DOCUMENTS

| | | |
|---|---|---|
| 0075065 | 3/1983 | European Pat. Off. . |
| 0127131 | 12/1984 | European Pat. Off. . |
| 3116087 | 11/1983 | Germany . |
| 3238394 | 4/1984 | Germany . |
| 1085367 | 3/1989 | Japan . |
| 1113302 | 5/1989 | Japan . |

OTHER PUBLICATIONS

Chemical Patents Index, Documentation Abstracts Journal, Section Ch, Week 8923, Aug. 2, 1989, Class C, AN 170489.

Chemical Patents Index, Documentation Abstracts Journal, Section Ch, Week 8919, Mar. 30, 1989, Class C, AN 140933.

*Primary Examiner*—Peter O'Sullivan
*Attorney, Agent, or Firm*—Millen, White, Zelano & Branigan

[57] ABSTRACT

A germicidal and fungicidal agent can solve the problems of conventional germicidal and fungicidal agents comprising quaternary ammonium salts or amphoteric surface active agents that fungicidal activity is insufficient and metals such as parts of medical instruments are corroded. Furthermore, it has higher germicidal and fungicidal activity against Gram-negative bacteria and filamentous fungi than benzalkonium chloride and excellent safety for human health. It is advantageously applied as a disinfectant for medical uses, a disinfectant for environment, a germicidal and fungicidal agent for fibers, a germicidal and fungicidal agent for cycling cooling water and the like. It has excellent resistance against discoloration, heat resistance, corrosion preventing property and compatibility with anionic surface active agents and can be used for providing all kinds of fibers with the germicidal and fungicidal activity to replace silicone type quaternary ammonium salts. The germicidal and fungicidal agent comprises quaternary ammonium salts having three alkyl or alkenyl groups connected to the nitrogen, an oxyalkylene group or its oligomer connected to the nitrogen and a counter ion which is an anion of a carboxylic acid, an ion of an alkyl ester of phosphoric acid or an ion of a polyoxyalkylenealkylether ester of phosphoric acid. A germicidal and fungicidal method utilizes the germicidal and fungicidal agent described above.

20 Claims, No Drawings

GERMICIDAL AND FUNGICIDAL AGENT AND A GERMICIDAL AND FUNGICIDAL METHOD

BACKGROUND OF THE INVENTION

1. Field of the Invention

The present invention relates to a novel germicidal and fungicidal agent. More particularly, it relates to a germicidal and fungicidal agent comprising a novel quaternary ammonium salt having sufficient germicidal and fungicidal activity to replace benzalkonium chloride and a germicidal and fungicidal method utilizing it.

2. Description of the Prior Art

Quaternary ammonium salts and amphoteric surface active agents, of which benzalkonium chloride and alkyldiaminoethylglycine hydrochloride are representative examples, have widely been used because they are relatively safe and have good germicidal activity.

However, these quaternary amine salts and amphoteric surface active agents have weak fungicidal activity and corrode metallic instruments and equipments. Moreover, when anionic surface active agents are present, they form insoluble complexes with the anionic surface active agents and the germicidal activity is decreased.

Application of benzalkonium chloride as a germicidal and fungicidal agent is naturally limited by these deficiencies. When dental devices are disinfected by using benzalkonium chloride, dicyclohexylamine nitrite or sodium nitrite is generally used together with benzalkonium chloride to prevent formation of rust on the devices used. However, sodium nitrite has a problem that it has carcinogenicity through the nirosation reaction and the use of this compound is not desirable. Dicyclohexylamine nitrite has not only the same problem of carcinogenicity as sodium nitrite but also another problem that insoluble precipitate is formed in the disinfectant solution because it has limited solubility in water.

Both of the germicidal and fungicidal activity and the rust preventing property are simultaneously required not only for the germicidal and fungicidal agents for medical uses but also for other germicidal and fungicidal agents which may be in contact with the human body, such as disinfectants for environments, germicidal and fungicidal agents for fibers and germicidal and fungicidal agents for cycling cooling water.

Cooling water used with cycling for cutting machines, air conditioners and the like is in conditions suited for propagation of germs and fungi. Corrosion preventing property is required for germicidal and fungicidal agents which are added to the cooling water for prevention of the propagation of such microorganisms. The germicidal and fungicidal agents of quaternary ammonium salt type are expected to become more widely utilized if they have sufficient corrosion preventing property because they exhibit little harmful effect for the human health.

Silicone type quaternary ammonium salts have been known as germicidal and fungicidal agents for fibers. This type of germicidal and fungicidal agents is generally applied for fiber treatment in combination with reactive silicone resins. Fiber products treated with the combined agents have problems, such as discoloration, decrease of fluorescent whiteness, decrease of water absorption, decomposition of the quaternary ammonium salt by heating, decrease of the germicidal activity by the decomposition, formation of rust in machines used for the treatment and the like other problems. It is inevitable that applications of the germicidal and fungicidal agents of this type are limited because of these problems.

Quaternary ammonium salts having the following formula have been proposed as the germicidal and fungicidal agents by the present inventors (Japanese Patent Publication Heisei 1-33589 and Heisei 3-35282):

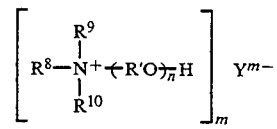

wherein $R^8$ is an alkyl group or alkenyl group having 8 to 22 carbon atoms, $R^9$ and $R^{10}$ are an alkyl group having 1 to 5 carbon atoms, respectively, $R'$ is an alkylene group having 2 to 4 carbon atoms, m is an integer of 1 or 2, n is an integer in the range from 1 to 5 and $Y^{m-}$ is an ion of an alkyl ester of phosphoric acid or an ion of a polyoxyethylenealkylether ester of phosphoric acid.

The germicidal and fungicidal agents proposed above have a problem that they do not have sufficient activity against Gram-negative bacteria even though they have sufficient activity against Gram-positive bacteria.

SUMMARY OF THE INVENTION

The present invention accordingly has an object to provide a germicidal and fungicidal agent which can solve the problems of the conventional germicidal and fungicidal agents of quaternary ammonium salts and amphoteric surface active agents, has a high germicidal and fungicidal activity against various kinds of bacteria including Gram-negative bacteria as well as Gram-positive bacteria, has little corrosive property against metallic apparatuses and instruments and is favorably utilized as a medical disinfectant, an environmental disinfectant, a germicidal and fungicidal agent for fibers and the like applications. The present invention has another object to provide a germicidal and fungicidal method having the similar characteristics as described above.

Extensive investigations were undertaken by the present inventors with the objects described above, in the course of which it was particularly mentioned that the conventional quaternary ammonium salts having germicidal activity, such as benzalkonium chloride, have a halogen ion as the counter ion and the halogen ion causes the corrosion and the decrease of heat stability, that the anionic surface active agents form the insoluble complexes not only with the cationic component but also with the counter anion of the germicidal and fungicidal agents and that the germicidal activity originates mainly from the structure of the cationic component. It was discovered that the objects can be achieved by a quaternary ammonium salt in which the counter ion is not an inorganic ion but an organic anion having the corrosion preventing property and the ability to increase the germicidal and fungicidal activity, such as an ion of an alkyl ester of phosphoric acid or an anion of a polyoxyalkylenealkylether ester of phosphoric acid, and an oxyalkylene group or its oligomer having an aryl group, a heteroaryl group or an aryloxy group with or without substituents is introduced on the nitrogen atom. It was also discovered that a quaternary ammonium salt in which an anion of a carboxylic acid is used as the anion and an oxyalkylene group or its oligomer is introduced on the nitrogen atom is more suitable for achieving the object. The present invention has been completed based on the discovery.

Thus, the germicidal and fungicidal agent of the invention comprises at least one compound selected from the group consisting of quaternary ammonium salts having the formula:

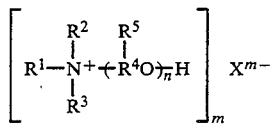

wherein $R^1$ is an alkyl group or an alkenyl group having 8 to 22 carbon atoms, $R^2$ is an alkyl group or an alkenyl group having 1 to 22 carbon atoms, $R^3$ is an alkyl group having 1 to 5 carbon atoms, $R^4$ is an alkylene group having 2 to 4 carbon atoms, $R^5$ is hydrogen or either one of an aryl group, a heteroaryl group and an aryloxy group with or without substituents, $X^{m-}$ is an anion of a carboxylic acid, an ion of an alkyl ester of phosphoric acid or an ion of a polyoxyalkylenealkylether ester of phosphoric acid, m is an integer in the range of 1 to 3 and n is an integer in the range of 1 to 5, $R^5$ being an aryl group, a heteroaryl group or an aryloxy group with or without substituents when $X^{m-}$ is an ion of an alkyl ester of phosphoric acid or an ion of a polyoxyalkylenealkylether ester of phosphoric acid having 1 to 12 carbon atoms.

The germicidal and fungicidal method of the invention utilizes the germicidal and fungicidal agent described above.

Other and further objects, features and advantages of the invention will appear more fully from the following description.

DETAILED DESCRIPTION OF THE INVENTION

The invention is described in detail in the following.

In the formula [1], $R^1$ is an alkyl group or an alkenyl group having 8 to 22 carbon atoms, preferably having 12 to 16 carbon atoms, and $R^2$ is an alkyl group or an alkenyl group having 1 to 22 carbon atoms, preferably having 1 to 4 carbon atoms.

In the same formula, $R^3$ is an alkyl group having 1 to 5 carbon atoms, preferably having 1 or 2 carbon atoms, and $R^4$ is an alkylene group having 2 to 4 carbon atoms, preferably having 2 or 3 carbon atoms.

The part $R^5$ is hydrogen or either one of an aryl group, a heteroaryl group and an aryloxy group with or without substituents, preferably an aryl group, a heteroaryl group or an aryloxy group with or without substituents and more preferably an aryloxy group with or without substituents.

The counter ion $X^{m-}$ is an anion of a carboxylic acid, an ion of an alkyl ester of phosphoric acid or an ion of a polyoxyalkylenealkylether ester of phosphoric acid having 1 to 12 carbon atoms, preferably an anion of a carboxylic acid having 2 to 10 carbon atoms and more preferably an anion of carboxylic acid having 4 to 8 carbon atoms.

The subscript and the superscript m is an integer in the range from 1 to 3, preferably 2 or 3 and more preferably 2 and the subscript n is an integer in the range from 1 to 5, preferably in the range from 1 to 3 and more preferably 1 or 2.

Examples of the group of $R^1$ in the formula [1] are: alkyl groups, such as octyl group, nonyl group, decyl group, undecyl group, dodecyl group, tridecyl group, tetradecyl group, pentadecyl group, hexadecyl group, heptadecyl group, octadecyl group, nonadecyl group and the like; and alkenyl groups, such as octenyl group, nonenyl group, decenyl group, undecenyl group, dodecenyl group, tetradecenyl group, pentadecenyl group, hexadecenyl group, heptadecenyl group and the like.

Examples of the group of $R^2$ in the formula [1] are: methyl group, ethyl group, propyl group, butyl group, pentyl group, hexyl group, octyl group, nonyl group, decyl group, undecyl group, dodecyl group, tridecyl group, tetradecyl group, pentadecyl group, hexadecyl group, heptadecyl group, octadecyl group, nonadecyl group and the like.

Examples of the group of $R^3$ are: methyl group, ethyl group, propyl group, butyl group and the like.

Examples of the group of $R^4O$ are:

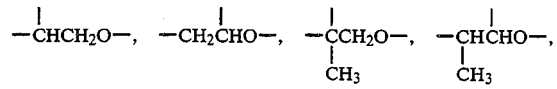

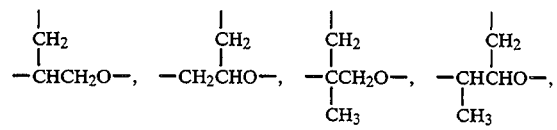

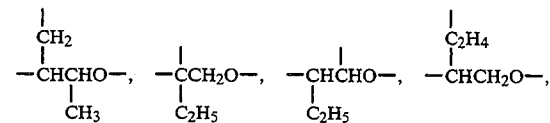

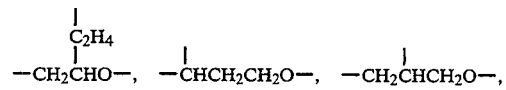

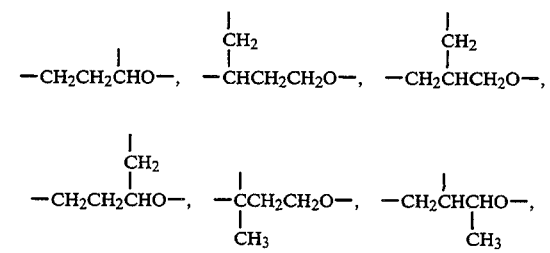

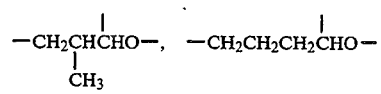

The group $R^5$ is hydrogen or either one of an aryl group, a heteroaryl group and an aryloxy group with or without substituents. When $X^{m-}$ is an ion of an alkyl ester of phosphoric acid or an ion of a polyoxyalkylenealkylether ester of phosphoric acid, $R^5$ is an aryl group, a heteroaryl group or an aryloxy group with or without substituents.

Examples of the aryl group in $R^5$ are phenyl group, naphthyl group and the like. Examples of the heteroaryl group in $R^5$ are pyridyl group, pyridinium group, quinolinium group and the like.

Examples of the substituents to the aryl group, the heteroaryl group or the aryloxy group are alkyl groups and alkoxy groups having 1 to 9 carbon atoms and halogen atoms, preferably alkyl groups having 1 to 9 carbon atoms, alkoxy groups having 1 to 4 carbon atoms and halogen atoms and more preferably methyl group and chlorine atom. More than one substituents may be introduced. The preferable number of substituent is 1 or 2.

Examples of the alkyl groups having 1 to 9 carbon atoms are methyl group, ethyl group, propyl group, butyl group, pentyl group, hexyl group, heptyl group, octyl group and nonyl group. Examples of the alkoxy groups having 1 to 9 carbon atoms are methoxy group, ethoxy group, propoxy group, butoxy group, pentoxy group, hexoxy group, heptoxy group, octoxy group and nonoxy group. Examples of the halogen atoms are chlorine atom, fluorine atom and bromine atom.

The counter ion $X^{m-}$ in the formula [1] is an ion of an alkyl ester of phosphoric acid, an ion of a polyoxyalkylenealkylether ester of phosphoric acid or an anion of a carboxylic acid having the functionality of 1 to 3.

When the counter ion $X^{m-}$ in the formula [1] is an ion of an alkyl ester of phosphoric acid or an ion of a polyoxyalkylenealkylether ester of phosphoric acid, at least one compound selected from the group consisting of alkyl esters of phosphoric acid and polyoxyalkylenealkylether esters of phosphoric acids having the following formula is utilized for the formation of the counter ion:

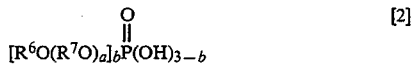

$$[R^6O(R^7O)_a]_bP(OH)_{3-b}$$

wherein $R^6$ is an alkyl group or an alkenyl group having 1 to 22 carbon atoms, $R^7$ is an alkylene group having 2 to 4 carbon atoms, a is 0 or an integer in the range from 1 to 10 and b is 1 (for a monoester of phosphoric acid) or 2 (for a diester of phosphoric acid).

Examples of the monoalkyl esters of phosphoric acid and the dialkyl esters of phosphoric acid are monoalkyl phosphates, such as monomethyl phosphate, monoethyl phosphate, mono-n-propyl phosphate, monoisopropyl phosphate, mono-n-butyl phosphate, monoisobutyl phosphate, mono-sec-butyl phosphate and the like; and dialkyl phosphates, such as dimethyl phosphate, diethyl phosphate, di-n-propyl phosphate, diisopropyl phosphate, di-n-butyl phosphate, diisobutyl phosphate, di-sec-butyl phosphate and the like. The alkyl esters of phosphoric acid may be used singly or as a combination of two or more kinds.

The kind of the carboxylic acid utilized for the anion of carboxylic acid which is the counter ion in the germicidal and fungicidal agent of the invention is not particularly limited so long as it is an organic acid which, in the form of a quaternary ammonium salt, does not exhibit corrosive property against metals. Examples of the carboxylic acid are acetic acid, lactic acid, maleic acid, fumaric acid, acrylic acid, methacrylic acid, citric acid, malic acid, tartaric acid, adipic acid, pimelic acid, suberic acid, azelaic acid, cebacic acid, dodecane-diacid- sorbic acid, undecylic acid, gluconic acid and the like; and salts of the carboxylic acids described above. Organic acids which form anions containing no halogen in the molecule when quaternary ammonium salts are prepared by using them are favorably utilized as the carboxylic acid in the invention.

Examples of the carboxylic acid particularly preferable for increasing the germicidal and fungicidal activity in the invention are maleic acid, fumaric acid, acrylic acid, methacrylic acid, citric acid, adipic and gluconic acid, sorbic acid, undecenoic acid and the like.

Some organic acids of 100% purity have corrosive property against metals at high temperatures. However, they lose the corrosive property when the purity is decreased. Organic acids generally have entirely no corrosive property against metals at the concentrations of application of the germicidal agents.

It is known that metabolic products of microorganisms have corrosive property against metals when the microorganisms propagate. Thus, the germicidal effect and the fungicidal effect are both effective for prevention of corrosion by themselves by preventing the propagation of the microorganisms.

The carboxylic acid may be utilized singly or as a combination of two or more kinds. It is preferable that adipic acid and sebacic acid is utilized in combination. The preferable ratio of adipic acid and sebacic acid in the combined use is in the range from 90: 10 to 10: 90.

In the quaternary ammonium salt of the invention, it is essential that an oxyalkylene group or an oligomer group thereof with or without substituents is introduced to the tertiary amine having the three groups, $R^1$, $R^2$ and $R^3$, as the fourth group in the quaternary ammonium salt for the purpose of increasing the germicidal activity.

For the introduction of oxyalkylene group with or without substituents, an epoxy compound, for example, is favorably utilized. Examples of the epoxy compound are ethylene oxide, propylene oxide, butylene oxide, styrene oxide, glycidyl pyridinium salt, phenyl glycidyl ether, methylphenyl glycidyl ether, ethylphenyl glycidyl ether, isopropylphenyl glycidyl ether, octylphenyl glycidyl ether, nonylphenyl glycidyl ether, 8-quinolyl glycidyl ether, chlorophenyl glycidyl ether and the like.

As the tertiary amine having the three groups, $R^1$, $R^2$ and $R^3$, described above, mono-(long chain alkyl)-di-(lower alkyl)-amines or di-(long chain alkyl)-mono-(lower alkyl)-amines are preferable.

Preferable examples of the mono-(long chain alkyl)-di-(lower alkyl)-amines are octyldimethylamine, octyldiethylamine, decyldimethylamine, decyldiethylamine, lauryldimethylarnine, lauryldiethylamine, myristyldimethylamine, myristyldiethylamine, palmityldimethylamine, palmityldiethylamine, stearyldimethylamine, stearyldiethylamine, oleyldimethylamine, oleyldiethylamine and the like. More preferable examples of the mono-(long chain alkyl)-di-(lower alkyl)-amines are lauryldimethylamine, myristyldimethylamine and palmityldimethylamine.

Preferable examples of the di-(long chain alkyl)-mono-(lower alkyl)-amines are dioctylmethylamine, dioctylethylamine, didecylmethylamine, didecylethylamine, dilaurylmethylamine, dilaurylethylamine, dimyristylmethylamine, dimyristylethylamine, dipalmitylmethylamine, dipalmitylethylamine, distearylmethylamine, distearylethylamine, dioleylmethylamine, dioleylethylamine and the like. More preferable examples of the di-(long chain alkyl)-mono-(lower alkyl)-amines are dioctylmethylamine, didecylmethylamine, dilaurylmethylamine and dimyristylmethylamine.

The quaternary ammonium salts may be utilized singly or as a combination of two or more kinds.

The method of preparation of the quaternary ammonium salts having the formula [1] is not particularly limited but conventional methods may be utilized. For example, to a tertiary amine, such as the mono-(long chain alkyl)-di-(lower alkyl)-amines or di-(long chain alkyl)-mono-(lower alkyl)-amines described above, an alkyl ester of phosphoric acid, a polyoxyalkylenealkylether ester of phosphoric acid or a carboxylic acid is added in an equivalent amount for neutralization and an aqueous solution of the neutralized product is prepared. The solution is then heated to a temperature generally in the range from 50° to 100° C., preferably in the range from 90° to 100° C. The epoxy compound described above is added for the reaction to the solution in an amount generally in the range from 1 to 5 moles, preferably in the range from 1 to 2 moles, per mole of the amine and the desired quaternary ammonium salt can be obtained.

The quaternary ammonium salt of the invention thus prepared has excellent germicidal and fungicidal activity, excellent corrosion preventing property even at the pH of 5.0 or above and can be advantageously utilized for various applications as the germicidal and fungicidal agent, such as medical disinfectant, environmental disinfectant, germicidal and fungicidal agent for fibers, germicidal and fungicidal agent for cycling cooling water and the like.

The quaternary ammonium salt of the invention may be utilized singly or as a combination of two or more kinds.

The amount to be used in the application of the germicidal and fungicidal agent of the invention is not particularly limited but may be suitably selected according to the application and the properties of the agent used. When it is used as a solution, the amount is generally in the range from 100 to 5,000 ppm and preferably in the range from 100 to 2,000 ppm.

When the germicidal and fungicidal agent of the invention is used for fibers, it can be used for treatment of all kinds of fiber, such as cotton, polyester/cotton fibers, polyester fibers, acrylic fibers, nylon fibers and the like. The method of the treatment is not particularly limited but may be selected and utilized suitably from the conventional methods, such as the continuous treatment, the dipping treatment, the spray treatment and the like.

Concentration of the germicidal and fungicidal agent of the invention applied to fibers is preferably selected in the range from 0.05 to 1% o.w.f. based on the fiber to be treated. When the concentration is less than 0.05 o.w.f., the treatment is insufficient for practical purposes and, when it is more than 1% o.w.f., the germicidal and fungicidal effect is not enhanced as expected from the higher concentration. The fibers treated by the germicidal and fungicidal agent of the invention have good resistance against laundering, show no discoloration and have excellent germicidal activity.

DESCRIPTION OF THE PREFERRED EMBODIMENTS

The invention will be understood more readily with reference to the following examples; however, these examples are intended to illustrate the invention and are not to be construed to limit the scope of the invention.

Properties of the germicidal and fungicidal agent were evaluated by the following methods.

(1) Measurement of corrosion preventing property

In a laboratory dish of 9 cm diameter, 4 sheets of gauze were laid on top of each other and 10 ml of 1% aqueous solution of a germicidal and fungicidal agent was added so that the sheets of gauze are immersed in the solution sufficiently. Ten setting pins were cleaned with acetone and laid on the sheets of gauze. After the setting pins were kept in contact with the solution for 48 hours at 45° C., the number of pins with corrosion was counted and expressed by the percentage to the total.

(2) Measurement of germicidal and fungicidal activity

Following bacteria were used as the test bacteria.
  *Klebsiella pneumoniae* IFO-13277
  Trichophyton mentagrophytes
  Penicillium citrinum The method of liquid medium dilution which is generally practiced is used as the test method and the effect of the germicidal and fungicidal agent was measured with varying time of contact with the bacteria. The germicidal and fungicidal activity was evaluated according to the following criteria.
  −: no growth of bacteria observed
  +: growth of bacteria observed In another method of evaluation, the minimum inhibition concentration (MIC) was measured by the method of agar plating dilution according to the method of Japanese Society of Chemical Therapy.

(3) Germicidal activity

A sample for testing was placed on an agar medium planted with bacillus pneumococcus and the bacteria was cultured for 24 hours at 37° C. The germicidal activity was evaluated by observing the growth of the bacteria in the area around the sample according to the following criteria.
  ○: no growth of the bacteria observed in the area around the sample; formation of halo observed.
  Δ: no formation of halo observed in the area around the sample; no growth of the bacteria observed on the top surface or the back surface of the sample.
  ×: growth of the bacteria observed on the top surface or the back surface of the sample.

(4) Discoloration

Sample fabrics were prepared by using cotton, T/C (mixed spun polyester/cotton) and PET (polyethylene terephthalate) by the methods described in Examples of Testing and discoloration was evaluated by the heat discoloration test (treated at 180° C. for 2 minutes), by the light fastness test (treated at 63° C. for 20 hours by using Fade-O-meter ®, manufactured by Suga Shikenki Co., Ltd.) and by the nitrogen oxide gas fastness test (according to the method of Japanese Industrial Standard L-0855).

Reflectance was measured on the treated sample fabrics by using a colorimeter (Macbeth COLOR - M2020 ®) and classified into the grades according to the method of Japanese Industrial Standard L-0804 (Grey scale for discoloration).

EXAMPLE OF PREPARATION OF MATERIAL 1

Into a reaction vessel, 68.1 weight parts of lauryldimethylamine, 21.6 weight parts of acrylic acid and 256 weight parts of water were charged and the mixture was neutralized. To the neutralized mixture, 20.0 weight parts of ethylene oxide were added and the mixture was allowed to react at 100° C. for 6 hours, to obtain a germicidal and fungicidal agent (1) of the invention.

EXAMPLE OF PREPARATION OF MATERIAL 2

Into a reaction vessel, 52 weight parts of octyldimethylamine, 55.2 weight parts of undecenoic acid and 180 weight parts of water were charged and the mixture was neutralized. To the neutralized mixture, 20.0 weight parts of ethylene oxide were added and the mixture was allowed to react at 100° C. for 6 hours, to obtain a germicidal and fungicidal agent (2) of the invention.

EXAMPLE OF PREPARATION OF MATERIAL 3

Into a reaction vessel, 98 weight parts of oleyldimethylamine, 17.4 weight parts of maleic acid and 199 weight parts of water were charged and the mixture was neutralized. To the neutralized mixture, 26.1 weight parts of propylene oxide were added and the mixture was allowed to react at 100° C. for 6 hours, to obtain a germicidal and fungicidal agent (3) of the invention.

EXAMPLE OF PREPARATION OF MATERIAL 4

Into a reaction vessel, 68.1 weight parts of myristyldimethylamine, 72 weight parts of sorbic acid and 230 weight parts of water were charged and the mixture was neutralized. To the neutralized mixture, 20.0 weight parts of ethylene oxide were added and the mixture was allowed to react at 100° C. for 6 hours, to obtain a germicidal and fungicidal agent (4) of the invention.

EXAMPLE OF PREPARATION OF MATERIAL 5

Into a reaction vessel, 68.1 weight parts of lauryldimethylamine, 72 weight parts of sorbic acid and 283 weight parts of water were charged and the mixture was neutralized. To the neutralized mixture, 32.4 weight parts of butylene oxide were added and the mixture was allowed to react at 100° C. for 6 hours, to obtain a germicidal and fungicidal agent (5) of the invention.

EXAMPLE OF PREPARATION OF MATERIAL 6

Into a reaction vessel, 89 weight parts of palmityldimethylamine, 72 weight parts of sorbic acid and 281 weight parts of water were charged and the mixture was neutralized. To the neutralized mixture, 26.1 weight parts of propylene oxide were added and the mixture was allowed to react at 100° C. for 6 hours, to obtain a germicidal and fungicidal agent (6) of the invention.

EXAMPLE OF PREPARATION OF MATERIAL 7

Into a reaction vessel, 110 weight parts of dilaurylmethylamine, 25.8 weight parts of methacrylic acid and 223 weight parts of water were charged and the mixture was neutralized. To the neutralized mixture, 20.0 weight parts of ethylene oxide were added and the mixture was allowed to react at 100° C. for 6 hours, to obtain a germicidal and fungicidal agent (7) of the invention.

EXAMPLE OF PREPARATION OF MATERIAL 8

Into a reaction vessel, 76.5 weight parts of dioctylmethylamine, 72 weight parts of sorbic acid and 249 weight parts of water were charged and the mixture was neutralized. To the neutralized mixture, 26.1 weight parts of propylene oxide were added and the mixture was allowed to react at 100° C. for 6 hours, to obtain a germicidal and fungicidal agent (8) of the invention.

EXAMPLE OF PREPARATION OF MATERIAL 9

Into a reaction vessel, 216 weight parts of lauryldimethylamine, 77 weight parts of adipic acid and 660 weight parts of water were charged and the mixture was neutralized. To the neutralized mixture, 185 weight parts of methylphenyl glycidyl ether were added and the mixture was allowed to react at 100° C. for 6 hours, to obtain a germicidal and fungicidal agent (9) of the invention.

EXAMPLE OF PREPARATION OF MATERIAL 10

Into a reaction vessel, 227 weight parts of an alkyldimethylamine (a mixture of 60 % of lauryldimethylamine, 35 % of myristyldimethylamine and 5% of palmityldimethylamine), 77 weight parts of adipic acid and 680 weight parts of water were charged and the mixture was neutralized. To the neutralized mixture, 170 weight parts of phenyl glycidyl ether were added and the mixture was allowed to react at 100° C. for 6 hours, to obtain a germicidal and fungicidal agent (10) of the invention.

EXAMPLE OF PREPARATION OF MATERIAL 11

Into a reaction vessel, 216 weight parts of lauryldimethylamine, 106 weight parts of sebacic acid and 710 weight parts of water were charged and the mixture was neutralized. To the neutralized mixture, 170 weight parts of phenyl glycidyl ether were added and the mixture was allowed to react at 100° C. for 6 hours, to obtain a germicidal and fungicidal agent (11) of the invention.

EXAMPLE OF PREPARATION OF MATERIAL 12

Into a reaction vessel, 216 weight parts of lauryldimethylamine, 15 weight parts of adipic acid, 81 weight parts of sebacic acid and 700 weight parts of water were charged and the mixture was neutralized. To the neutralized mixture, 160 weight parts of phenyl glycidyl ether were added and the mixture was allowed to react at 100° C. for 6 hours, to obtain a germicidal and fungicidal agent (12) of the invention.

EXAMPLE OF PREPARATION OF MATERIAL 13

Into a reaction vessel, 216 weight parts of lauryldimethylamine, 15 weight parts of adipic acid, 115 weight parts of dodecanedicarboxylic acid and 760 weight parts of water were charged and the mixture was neutralized. To the neutralized mixture, 160 weight parts of phenyl glycidyl ether were added and the mixture was allowed to react at 100° C. for 6 hours, to obtain a germicidal and fungicidal agent (13) of the invention.

EXAMPLE OF PREPARATION OF MATERIAL 14

Into a reaction vessel, 68.1 weight parts of lauryldimethylamine, 17.8 weight parts of succinic acid and 200 weight parts of water were charged and the mixture was neutralized. To the neutralized mixture, 49.5 weight parts of phenyl glycidyl ether were added and the mixture was allowed to react at 100° C. for 6 hours, to obtain a germicidal and fungicidal agent (14) of the invention.

EXAMPLE OF PREPARATION OF MATERIAL 15

Into a reaction vessel, 52 weight parts of octyldimethylamine, 22 weight parts of adipic acid and 200 weight parts of water were charged and the mixture was neutralized. To the neutralized mixture, 49.5 weight parts of phenyl glycidyl ether were added and the mixture was allowed to react at 100° C. for 6 hours, to obtain a germicidal and fungicidal agent (15) of the invention.

EXAMPLE OF PREPARATION OF MATERIAL 16

Into a reaction vessel, 98 weight parts of oleyldimethylamine, 17.4 weight parts of maleic acid and 200 weight parts of water were charged and the mixture was neutralized. To the neutralized mixture, 49.5 weight parts of phenyl glycidyl ether were added and the mixture was allowed to react at 100° C. for 6 hours, to obtain a germicidal and fungicidal agent (16) of the invention.

EXAMPLE OF PREPARATION OF MATERIAL 17

Into a reaction vessel, 68.1 weight parts of myristyldimethylamine, 17.4 weight parts of fumaric acid and 200 weight parts of water were charged and the mixture was neutralized. To the neutralized mixture, 49.5 weight parts of phenyl glycidyl ether were added and the mixture was allowed to react at 100° C. for 6 hours, to obtain a germicidal and fungicidal agent (17) of the invention.

EXAMPLE OF PREPARATION OF MATERIAL 18

Into a reaction vessel, 68.1 weight parts of lauryldimethylamine, 22.5 weight parts of tartaric acid and 200 weight parts of water were charged and the mixture was neutralized. To the neutralized mixture, 49.5 weight parts of phenyl glycidyl ether were added and the mixture was allowed to react at 100° C. for 6 hours, to obtain a germicidal and fungicidal agent (18) of the invention.

EXAMPLE OF PREPARATION OF MATERIAL 19

Into a reaction vessel, 89 weight parts of palmityldimethylamine, 34 weight parts of 85~92% lactic acid and 200 weight parts of water were charged and the mixture was neutralized. To the neutralized mixture, 49.5 weight parts of phenyl glycidyl ether were added and the mixture was allowed to react at 100° C. for 6 hours, to obtain a germicidal and fungicidal agent (19) of the invention.

EXAMPLE OF PREPARATION OF MATERIAL 20

Into a reaction vessel, 68.1 weight parts of lauryldimethylamine, 19.2 weight parts of citric acid and 200 weight parts of water were charged and the mixture was neutralized. To the neutralized mixture, 49.5 weight parts of phenyl glycidyl ether were added and the mixture was allowed to react at 100° C. for 6 hours, to obtain a germicidal and fungicidal agent (20) of the invention.

EXAMPLE OF PREPARATION OF MATERIAL 21

Into a reaction vessel, 52 weight parts of octyldimethylamine, 72 weight parts of sorbic acid and 200 weight parts of water were charged and the mixture was neutralized. To the neutralized mixture, 49.5 weight parts of phenyl glycidyl ether were added and the mixture was allowed to react at 100° C. for 6 hours, to obtain a germicidal and fungicidal agent (21) of the invention.

EXAMPLE OF PREPARATION OF MATERIAL 22

Into a reaction vessel, 68.1 weight parts of lauryldimethylamine, 17.8 weight parts of succinic acid and 200 weight parts of water were charged and the mixture was neutralized. To the neutralized mixture, 52.8 weight parts of glycidylpyridinium chloride were added and the mixture was allowed to react at 100° C. for 6 hours, to obtain a germicidal and fungicidal agent (22) of the invention.

EXAMPLE OF PREPARATION OF MATERIAL 23

Into a reaction vessel, 68.1 weight parts of lauryldimethylamine, 17.8 weight parts of succinic acid and 200 weight parts of water were charged and the mixture was neutralized. To the neutralized mixture, 36 weight parts of styrene oxide was added and the mixture was allowed to react at 100° C. for 6 hours, to obtain a germicidal and fungicidal agent (23) of the invention.

EXAMPLE OF TESTING 1

Germicidal activities and corrosion preventing properties of the germicidal and fungicidal agents of the invention prepared above and benzalkonium chloride were evaluated. Results of the evaluation are shown in Table I to Table 3.

When the results of the evaluation of the germicidal and fungicidal agents of the invention are compared with those of benzalkonium chloride, the advantage of the agents of the invention is obvious. The germicidal activity of the agents of the invention against Gram-negative bacteria is also higher than that of benzalkonium chloride.

EXAMPLE OF PREPARATION OF MATERIAL 24

Into a reaction vessel, 32 weight parts of isopropyl phosphate containing the monoester and the diester in about 1/1 weight ratio which was prepared from 18 weight parts of isopropanol and 14 weight parts of anhydrous phosphoric acid and 140 weight parts of water were charged, then, 34 weight parts of lauryldimethylamine were added and the mixture was neutralized. To the neutralized mixture, 15 weight parts of phenyl glycidyl ether were added and the mixture was allowed to react at 100° C. for 3 hours, to obtain a germicidal and fungicidal agent (24) of the invention.

The agent prepared above had good compatibility with salts of laurylsulfuric acid and showed an excellent feature that it had the properties of an amphoteric surface active agent even though it was actually a cationic surface active agent.

EXAMPLE OF PREPARATION OF MATERIAL 25

Into a reaction vessel, 32 weight parts of isopropyl phosphate containing the monoester and the d/ester in about 1/1 weight ratio which was prepared from 18 weight parts of isopropanol and 14 weight parts of anhydrous phosphoric acid and 156 weight parts of water were charged, then 34 weight parts of lauryldimethylamine were added and the mixture was neutralized. To the neutralized mixture, 12 weight parts of styrene oxide were added and the mixture was allowed to react at 100° C. for 3 hours, to obtain a germicidal and fungicidal agent (25) of the invention.

The agent prepared above had good compatibility with salts of laurylsulfuric acid and showed an excellent feature that it had the properties of an amphoteric surface active agent even though it was actually a cationic surface active agent.

EXAMPLE OF PREPARATION OF MATERIAL 26

Into a reaction vessel, 24 weight parts of methyl phosphate containing the monoester and the diester in about 1/1 ratio which was prepared from 10 weight parts of methyl alcohol and 14 weight parts of anhydrous phosphoric acid and 146 weight parts of water were charged, then 34 weight parts of lauryldimethylamine were added and the mixture was neutralized. To the neutralized mixture, 15 weight parts of phenyl glycidyl ether were added and the mixture was allowed to react at 100° C. for 3 hours, to obtain a germicidal and fungicidal agent (26) of the invention.

The agent prepared above had good compatibility with salts of laurylsulfuric acid and showed an excellent feature that it had the properties of an amphoteric surface active agent even though it was actually a cationic surface active agent.

EXAMPLE OF PREPARATION OF MATERIAL 27

Into a reaction vessel, 36 weight parts of butyl phosphate containing the monoester and the diester in about 1/1 ratio which was prepared from 22 weight parts of butyl alcohol and 14 weight parts of anhydrous phosphoric acid and 170 weight parts of water were charged, then 34 weight parts of lauryldimethylamine were added and the mixture was neutralized. To the neutralized mixture, 15 weight parts of phenyl glycidyl ether were added and the mixture was allowed to react at 100° C. for 3 hours, to obtain a germicidal and fungicidal agent (27) of the invention.

The agent prepared above had good compatibility with salts of laurylsulfuric acid and showed an excellent feature that it had the properties of an amphoteric surface active agent even though it was actually a cationic surface active agent.

EXAMPLE OF TESTING 2

A sheet of cotton broad cloth (No. 40 count) was treated with a 0.1 weight % solution of one of the germicidal and fungicidal agents of the invention prepared in Examples of Preparation of Material 24 to 27, with a 0.1 weight % solution of benzalkonium chloride or with a 1.0 weight % solution of a silicone type quaternary ammonium salt in the condition of 100% squeezing. The treated sheet of cloth was dried at 105° C. for 3 minutes and cured at 160° C. for 2 minutes. Germicidal activity was evaluated on the sample sheet of the cloth thus prepared in the conditions of no laundering, 10 times laundering, 20 times laundering and 30 times laundering. Results of the evaluation are shown in Table 4.

The laundering was conducted as following. A sample sheet of the cloth was placed in a household electric washer, washed 5 minutes with water of 40° C. containing 2 g/l of a neutral detergent New Beads ® (a product of Kao Corporation, Ltd.), washed with fresh running water for 2 minutes, dehydrated, washed with fresh running water for 2 minutes, dehydrated and dried. This operation was repeated as designated.

EXAMPLE OF TESTING 3

Testing was conducted in the same way as in Example of Testing 2 except that a sheet of polyester/cotton (65/35 weight ratio) broad cloth was used in place of a sheet of cotton broad cloth. Results of the evaluation of the germicidal activity are shown in Table 4.

EXAMPLE OF TESTING 4

Testing was conducted in the same way as in Example of Testing 2 except that a sheet of polyester jersey cloth was used in place of a sheet of cotton broad cloth and that the treated sheet of cloth was cured at 180° C. for 30 seconds in place of curing at 160° C. for 2 minutes. Results of the evaluation of the germicidal activity are shown in Table 4.

EXAMPLE OF TESTING 5

Corrosion preventing properties of the germicidal and fungicidal agents prepared in Examples of Preparation of Material 24 to 27, benzalkonium chloride and a silicone type quaternary ammonium salt were evaluated. Results of the evaluation are shown in Table 5.

EXAMPLE OF TESTING 6

Heat discoloration test, light fastness test and nitrogen oxide gas fastness test of the germicidal and fungicidal agents prepared in Examples of Preparation of Material 24 to 27, benzalkonium chloride and a silicone type quaternary ammonium salt were made and the resistances against discoloration were evaluated. Results of the evaluation are shown in Table 6.

EXAMPLE OF TESTING 7

Germicidal activities against Gram-negative bacteria of germicidal and fungicidal agents prepared in Examples of Preparation of Material 24 to 27, benzalkonium chloride and an agent described in Japanese Patent Publication Heisei 1-33589 were evaluated. Results of the evaluation are shown in Table 7.

EXAMPLE OF PREPARATION OF MATERIAL 28

Into a reaction vessel, 28 weight parts of ethyl phosphate prepared from 14 weight parts of ethyl alcohol and 14 weight parts of anhydrous phosphoric acid and 154 weight parts of water were charged, then 34 weight parts of lauryldimethylamine were added and the mixture was neutralized. To the neutralized mixture, 15 weight parts of phenyl glycidyl ether were added and the mixture was allowed to react at 100° C. for 3 hours, to obtain a germicidal and fungicidal agent (28) of the invention.

EXAMPLE OF PREPARATION OF MATERIAL 29

Into a reaction vessel, 41 weight parts of ethoxyethyl phosphate prepared from 27 weight parts of ethylcellosolve and 14 weight parts of anhydrous phosphoric acid and 180 weight parts of water were charged, then 34 weight parts of lauryldimethylamine were added and the mixture was neutralized. To the neutralized mixture, 15 weight parts of phenyl glycidyl ether were added and the mixture was allowed to react at 100° C. for 3 hours, to obtain a germicidal and fungicidal agent (29) of the invention.

EXAMPLE OF PREPARATION OF MATERIAL 30

Into a reaction vessel, 28 weight parts of ethyl phosphate prepared from 14 weight parts of ethyl alcohol and 14 weight parts of anhydrous phosphoric acid and 74 weight parts of water were charged, then 34 weight parts of lauryldimethylamine were added and the mixture was neutralized. To the neutralized mixture, 12 weight parts of styrene oxide were added and the mixture was allowed to react at 100° C. for 3 hours, to obtain a germicidal and fungicidal agent (30) of the invention.

EXAMPLE OF PREPARATION OF MATERIAL 31

Into a reaction vessel, 28 weight parts of ethyl phosphate prepared from 14 weight parts of ethyl alcohol and 14 weight parts of anhydrous phosphoric acid and 81 weight parts of water were charged, then 38 weight parts of dioctylmethylamine were added and the mixture was neutralized. To the neutralized mixture, 15 weight parts of phenyl glycidyl ether were added and the mixture was allowed to react at 100° C. for 3 hours, to obtain a germicidal and fungicidal agent (31) of the invention.

EXAMPLE OF PREPARATION OF MATERIAL 32

Into a reaction vessel, 28 weight parts of ethyl phosphate prepared from 14 weight parts of ethyl alcohol and 14 weight parts of anhydrous phosphoric acid and 72 weight parts of water were charged, then 24 weight parts of octyldimethylamine were added and the mixture was neutralized. To the neutralized mixture, 20 weight parts of 8-quinolyl glycidyl ether were added and the mixture was allowed to react at 100° C. for 3 hours, to obtain a germicidal and fungicidal agent (32) of the invention.

EXAMPLE OF TESTING 8

Germicidal activities, corrosion preventing properties and compatibilities with an anionic surface active agent ABSNa (sodium alkylbenzenesulfonate) of the germicidal and fungicidal agents prepared in Examples of Preparation of Material 24 and 26 to 32 and benzalkonium chloride were evaluated. Results of the evaluation are shown in Table 8.

While the invention has been particularly shown and described with reference to preferred embodiments thereof, it will be understood by those skilled in the art that the foregoing and other changes in form and details can be made therein without departing from the spirit and scope of the invention.

To summarize the advantages obtained by the invention, the germicidal and fungicidal agent of the invention can solve the problems of conventional germicidal and fungicidal agents comprising quaternary ammonium salts or amphoteric surface active agents that fungicidal activity is insufficient and metals such as parts of medical instruments are corroded. Furthermore, it has higher germicidal and fungicidal activity against Gram-negative bacteria and filamentous fungi than benzalkonium chloride and excellent safety for human health. It is advantageously applied as a disinfectant for medical uses, a disinfectant for environment, a germicidal and fungicidal agent for fibers, a germicidal and fungicidal agent for cycling cooling water and the like. It has excellent resistance against discoloration, heat resistance, corrosion preventing property and compatibility with anionic surface active agents and can be used for providing all kinds of fibers, such as cotton, polyester cotton, polyester fibers, acrylic fibers, nylon fibers and the like, with the germicidal and fungicidal activity to replace silicone type quaternary ammonium salts.

TABLE 1

| | concentration of germicidal and fungicidal agent (ppm) | | | corrosion preventing property |
|---|---|---|---|---|
| | K. pneumoniae | T. mentagrophytes | P. citrinum | (% corrosion) |
| germicidal and fungicidal agent (1) | 50 | 1000 | 1000 | 0 |
| germicidal and fungicidal agent (2) | 50 | 200 | 200 | 0 |
| germicidal and fungicidal agent (3) | 50 | 500 | 500 | 0 |
| germicidal and fungicidal agent (4) | 50 | 100 | 100 | 0 |
| germicidal and fungicidal agent (5) | 50 | 100 | 100 | 0 |
| germicidal and fungicidal agent (6) | 50 | 100 | 100 | 0 |
| germicidal and fungicidal agent (7) | 100 | 1000 | 1000 | 0 |
| germicidal and fungicidal agent (8) | 100 | 1000 | 1000 | 0 |
| benzalkonium chloride[1] | 100 | 1000 | 1000 | 100 |

[1] A comparative example

TABLE 2

| | concentration of germicidal and fungicidal agent (ppm) | | | corrosion preventing property |
|---|---|---|---|---|
| | K. pneumoniae | T. mentagrophytes | P. citrinum | (% corrosion) |
| germicidal and fungicidal agent (9) | 50 | 1000 | 1000 | 0 |
| germicidal and fungicidal agent (10) | 25 | 200 | 200 | 0 |
| germicidal and fungicidal agent (11) | 25 | 200 | 200 | 0 |
| germicidal and fungicidal agent (12) | 25 | 100 | 100 | 0 |
| germicidal and fungicidal | 50 | 100 | 100 | 0 |

TABLE 2-continued

| | concentration of germicidal and fungicidal agent (ppm) | | | corrosion preventing property (% corrosion) |
|---|---|---|---|---|
| | K. pneumoniae | T. mentagrophytes | P. citrinum | |
| agent (13) | | | | |
| benzalkonium chloride[1] | 100 | 1000 | 1000 | 100 |

[1]A comparative example

TABLE 3

| | time of contact (minute) | concentration of germicidal and fungicidal agent (ppm) | | | | | | corrosion preventing property (% corrosion) |
|---|---|---|---|---|---|---|---|---|
| | | 0.1 | 0.05 | 0.025 | 0.0125 | 0.0063 | 0.0032 | |
| germicidal and fungicidal agent (14) | 2.5 | − | − | − | − | + | + | 0 |
| germicidal and fungicidal agent (15) | 2.5 | − | − | + | + | + | + | 0 |
| germicidal and fungicidal agent (16) | 2.5 | − | − | − | + | + | + | 0 |
| germicidal and fungicidal agent (17) | 2.5 | − | − | − | − | + | + | 0 |
| germicidal and fungicidal agent (18) | 2.5 | − | − | − | − | + | + | 0 |
| germicidal and fungicidal agent (19) | 2.5 | − | − | − | + | + | + | 0 |
| germicidal and fungicidal agent (20) | 2.5 | − | − | − | − | + | + | 0 |
| germicidal and fungicidal agent (21) | 2.5 | − | − | + | + | + | + | 0 |
| germicidal and fungicidal agent (22) | 2.5 | − | − | − | − | + | + | 0 |
| germicidal and fungicidal agent (23) | 2.5 | − | − | − | + | + | + | 0 |
| benzalkonium chloride[1] | 2.5 | − | − | + | + | + | + | 100 |

[1]A comparative example

TABLE 5

| germicidal and fungicidal agent | formation of rust (%) |
|---|---|
| germicidal and fungicidal agent (24) | 0 |
| germicidal and fungicidal agent (25) | 0 |
| germicidal and fungicidal agent (26) | 0 |
| germicidal and fungicidal agent (27) | 0 |
| benzalkonium chloride[1] | 100 |
| silicone type quaternary ammonium salt[1] | 100 |

[1]Comparative examples

TABLE 4

| germicidal and fungicidal agent | | Example of Testing 2 cotton broad cloth | | | |
|---|---|---|---|---|---|
| kind | concentration (wt. %) | L-0 | L-10 | L-20 | L-30[2] |
| germicidal and fungicidal agent (24) | 0.1 | ○ | ○ | △ | X |
| germicidal and fungicidal agent (25) | 0.1 | ○ | ○ | △ | X |
| germicidal and fungicidal agent (26) | 0.1 | ○ | ○ | △ | X |
| germicidal and fungicidal agent (27) | 0.1 | ○ | ○ | △ | X |
| benzalkonium chloride[1] | 0.1 | ○ | X | X | X |
| silicone type quaternary ammonium salt[1] | 1.0 | X | X | X | X |

| germicidal and fungicidal agent | Example of Testing 3 polyester/cotton (65/35) | | | | Example of Testing 4 polyester | | | |
|---|---|---|---|---|---|---|---|---|
| | L-0 | L-10 | L-20 | L-30[2] | L-0 | L-10 | L-20 | L-30[2] |
| germicidal and fungicidal agent (24) | ○ | ○ | △ | X | ○ | ○ | △ | X |
| germicidal and fungicidal agent (25) | ○ | ○ | △ | X | ○ | ○ | △ | X |
| germicidal and fungicidal agent (26) | ○ | ○ | △ | X | ○ | ○ | △ | X |
| germicidal and fungicidal agent (27) | ○ | ○ | △ | X | ○ | ○ | △ | X |
| benzalkonium chloride[1] | ○ | △ | X | X | ○ | ○ | △ | X |
| silicone type quaternary ammonium salt[1] | X | X | X | X | X | X | X | X |

[1]Comparative examples
[2]L-0, L-10, L-20 and L-30 mean no laundering, 10, 20 and 30 launderings, respectively.

TABLE 6

| germicidal and fungicidal agent | heat discoloration test | | | light fastness test | | | nitrogen oxide gas fastness test | | |
|---|---|---|---|---|---|---|---|---|---|
| | cotton | T/C | PET | cotton | T/C | PET | cotton | T/C | PET[2] |
| germicidal and fungicidal agent (24) | 4 | 4 | 4 | 4–5 | 4–5 | 4–4 | 5 | 5 | 5 |
| germicidal and fungicidal agent (25) | 3 | 3 | 3 | 3–4 | 3–4 | 3–4 | 4–5 | 4–5 | 4–5 |
| germicidal and fungicidal agent (26) | 4 | 4 | 4 | 4–5 | 4–5 | 4–5 | 5 | 5 | 5 |
| germicidal and fungicidal agent (27) | 4 | 4 | 4 | 4–5 | 4–5 | 4–5 | 5 | 5 | 5 |
| benzalkonium chloride[1] | 2 | 2 | 2 | 3–4 | 3–4 | 3–4 | 4 | 4 | 4 |
| silicone type quaternary ammonium salt[1] | 2 | 2 | 2 | 4 | 4 | 4 | 4 | 4–5 | 4 |

[1] Comparative examples
[2] T/C: mixed spun polyester/cotton; PET: polyethylene terephthalate

TABLE 7

| | time of contact[1] (minute) | concentration of germicidal and fungicidal agent (weight %) | | | | | |
|---|---|---|---|---|---|---|---|
| | | 0.2 | 0.1 | 0.05 | 0.025 | 0.0125 | 0.0063 |
| germicidal and fungicidal agent (24) | 2.5 | − | − | − | − | − | + |
| germicidal and fungicidal agent (25) | 2.5 | − | − | − | − | − | + |
| germicidal and fungicidal agent (26) | 2.5 | − | − | − | − | − | + |
| germicidal and fungicidal agent (27) | 2.5 | − | − | − | − | − | + |
| benzalkonium chloride[2] | 2.5 | − | − | − | + | + | + |
| the agent described in Jap. Pat. Publ. Heisei 1-33589[2] | 2.5 | − | + | + | + | + | + |

[1] Bacteria used: *Klebsiella pneumoniae* IFO 13277
[2] Comparative examples

TABLE 8

| | germicidal activity | | | | | | | |
|---|---|---|---|---|---|---|---|---|
| | time of contact (minute) | concentration of germicidal and fungicidal agent (weight %) | | | | | | corrosion resistance (% corrosion) | compatibility with ABSNa |
| | | 0.1 | 0.05 | 0.025 | 0.0125 | 0.0063 | 0.0032 | | |
| germicidal and fungicidal agent (24) | 2.5 | − | − | − | − | + | + | 0 | compatible |
| germicidal and fungicidal agent (26) | 2.5 | − | − | − | − | + | + | 0 | compatible |
| germicidal and fungicidal agent (27) | 2.5 | − | − | − | − | + | + | 0 | compatible |
| germicidal and fungicidal agent (28) | 2.5 | − | − | − | − | + | + | 0 | compatible |
| germicidal and fungicidal agent (29) | 2.5 | − | − | − | − | + | + | 0 | compatible |
| germicidal and fungicidal agent (30) | 2.5 | − | − | − | − | + | + | 0 | compatible |
| germicidal and fungicidal agent (31) | 2.5 | − | + | + | + | + | + | 0 | compatible |
| germicidal and fungicidal agent (32) | 2.5 | − | + | + | + | + | + | 0 | compatible |
| benzalkonium chloride[1] | 2.5 | − | − | + | + | + | + | 100 | precipitate |

[1] A comparative example

What is claimed is:

1. A germidical and fungicidal agent which comprises at least one compound selected from the group consisting of quaternary ammonium salts having the formula:

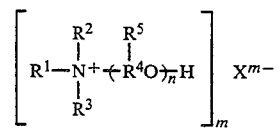

wherein $R^1$ is an alkyl group or an alkenyl group having 8 to 22 carbon atoms, $R^2$ is an alkyl group having 1 to 22 carbon atoms or an alkenyl group having 2 to 22 carbon atoms, $R^3$ is an alkyl group having 1 to 5 carbon atoms, $R^4$ is an alkylene group having 2 to 4 carbon atoms, $R^6$ is hydrogen or either one of an aryl group, a heteroaryl group and an arloxy group with or without substituents, $X^{m-}$ is an anion of a carboxylic acid, an ion of an alkyl ester of phosphoric acid or an ion of a polyoxyalkylenealkylether ester of phosphoric acid having 1 to 12 carbon atoms, m is an integer from 1 to 3 and n is an integer from 1 to 5, $R^5$ being an aryl group, a heteroaryl group or an arloxy group with or without substituents when $X^{m-}$ is an ion of an alkyl ester of phosphoric acid or an ion of a polyoxyalkylenenalkylether ester of phosphoric acid.

2. A germicidal and fungicidal agent as claimed in claim 1 wherein $X^{m-}$ is an anion of a carboxylic acid.

3. A germicidal and fungicidal agent as claimed in claim 1 wherein $X^{m-}$ is an anion of a carboxylic acid containing no halogen in the molecule.

4. A germicidal and fungicidal agent as claimed in claim 1 wherein $X^{m-}$ is an anion of at least one compound selected from the group consisting of acetic acrid, lactic acid, maleic acid, fumaric acid, acrylic acid, methacrylic acid, citric acid, malic acid, tartaric acid, adipic acid, pimelic acid, suberic acid, azelaic acid, cebacic acid, dodecane-diacid, sorbic acid, undecylic acid and gluconic acid.

5. A germicidal and fungicidal agent as claimed in claim 1 wherein $X^{m-}$ is an anion of at least one compound selected from the group consisting of maleic acid, fumaric acid, acrylic acid, methacrylic acid, citric acid, adipic acid, sorbic acid, undecylic acid and gluconic acid.

6. A germicidal and fungicidal agent as claimed in claim 1 wherein $X^{m-}$ are anions of adipic acid and sebacic acid in the range from 90:10 to 10:90 by weight.

7. A germicidal and fungicidal agent as claimed in claim 1 wherein $R^1$ is an alkyl group or an alkenyl group having 12 to 16 carbon atoms.

8. A germicidal and fungicidal agent as claimed in claim 1, wherein $R^2$ is an alkyl group having 1 to 4 carbon atoms or an alkenyl group having 2 to 4 carbon atoms.

9. A germicidal and fungicidal agent as claimed in claim 1 wherein $R^3$ is an alkyl group having 1 to 2 carbon atoms.

10. A germicidal and fungicidal agent as claimed in claim 1, wherein $R^5$ is an aryloxy group with or without substituents.

11. A germidical and fungicidal method which comprises treating a substance with a germicidal or fungicidal effective amount of a germicidal and fungicidal agent comprising at least one compound selected from the group consisting of quaternary ammonium salts having the formula:

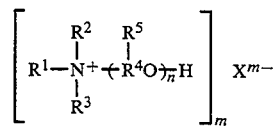

wherein $R^1$ is an alkyl group or an alkenyl group having 8 to 22 carbon atoms, $R^2$ is an alkyl group having 1 to 22 carbon atoms or an alkenyl group having 2 to 22 carbon atoms, $R^3$ is an alkyl group having 1 to 5 carbon atoms, $R^4$ is an alkylene group having 2 to 4 carbon atoms, $R^5$ is hydrogen or either one of an aryl group, a heteroaryl group and an arloxy group with or without substituents, $X^{m-}$ is an anion of a carboxylic acid, an ion of an alkyl ester of phosphoric acid or an ion of a polyoxyalkylenealkylether ester of phosphoric acid having 1 to 12 carbon atoms, m is an integer from 1 to 3 and n is an integer from 1 to 5, $R^5$ being an aryl group, a heteroaryl group or an arloxy group with or without substituents when $X^-$ is an ion of an alkyl ester of phosphoric acid or an ion of a polyoxyalkylenenalkylether ester of phosphoric acid.

12. A germicidal and fungicidal method as claimed in claim 11 wherein $X^{m-}$ is an anion of a carboxylic acid.

13. A germicidal and fungicidal method as claimed in claim 11 wherein $X^{m-}$ is an anion of a carboxylic acid containing no halogen in the molecule.

14. A germicidal and fungicidal method as claimed in claim 11 wherein X is an anion of at least one compound selected from the group consisting of acetic acid, lactic acid, maleic acid, fumaric acid, acrylic acid, methacrylic acid, citric acid, malic acid, tartaric acid, adipic acid, pimelic acid, suberic acid, azelaic acid, cebacic acid, dodecane-diacid, sorbic acid, undecylic acid and gluconic acid.

15. A germicidal and fungicidal method as claimed in claim 11 wherein $X^{m-}$ is an anion of at least one compound selected from the group consisting of maleic acid, fumaric acid, acrylic acid, methacrylic acid, citric acid, adipic acid, sorbic acid, undecylic acid and gluconic acid.

16. A germicidal and fungicidal method as claimed in claim 11 wherein $X^{m-}$ are anions of adipic acid and sebacic acid in the range from 90:10 to 10:90 by weight.

17. A germicidal and fungicidal method as claimed in claim 11 wherein $R^1$ is an alkyl group or an alkenyl group having ]2 to ]6 carbon atoms.

18. A germicidal and fungicidal method as claimed in claim 16, wherein $R^2$ is an alkyl group having 1 to 4 carbon atoms or an alkenyl group having 11 to 4 carbon atoms.

19. A germicidal and fungicidal method as claimed in claim 11 wherein $R^3$ is an alkyl group having 1 to 2 carbon atoms.

20. A germicidal and fungicidal method as claimed in claim 11 wherein $R^5$ is an aryloxy group with or without substituents.

* * * * *

UNITED STATES PATENT AND TRADEMARK OFFICE
CERTIFICATE OF CORRECTION

PATENT NO. : 5,362,910
DATED : November 08, 1994
INVENTOR(S) : Masahiro MAKINO et al.

It is certified that error appears in the above-indentified patent and that said Letters Patent is hereby corrected as shown below:

Claim 1, Column 21, Line 5:  Delete "$R^6$" and insert -- $R^5$ --.

Claim 14, Column 22, Line 31:  After "X" add -- $^m$ --.

Claim 17, Column 22, Line 49:  Change "$J2$ to $J6$" to read . . .    -- 12 to 16 --.

Signed and Sealed this

Thirty-first Day of January, 1995

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,362,910
DATED : November 08, 1994
INVENTOR(S) : Masahiro MAKINO et al.

It is certified that error appears in the above-identified patent and that said Letters Patent is hereby corrected as shown below:

Claim 18, Column 22, Line 52: Delete "11" and insert - - 2 - - .

Signed and Sealed this

Seventh Day of March, 1995

*Attest:*

BRUCE LEHMAN

*Attesting Officer*     *Commissioner of Patents and Trademarks*